United States Patent
Ross et al.

(10) Patent No.: US 9,839,376 B1
(45) Date of Patent: Dec. 12, 2017

(54) SYSTEMS AND METHODS FOR AUTOMATED BODY MASS INDEX CALCULATION TO DETERMINE VALUE

(71) Applicant: Massachusetts Mutual Life Insurance Company, Springfield, MA (US)

(72) Inventors: Gareth Ross, Amherst, MA (US); Yaron Ben-Zvi, Hastings on Hudson, NY (US); Sears Merritt, Groton, MA (US)

(73) Assignee: Massachusetts Mutual Life Insurance, Springfield, MA (US)

( * ) Notice: Subject to any disclaimer, the term of this patent is extended or adjusted under 35 U.S.C. 154(b) by 55 days.

(21) Appl. No.: 15/134,080

(22) Filed: Apr. 20, 2016

Related U.S. Application Data

(60) Provisional application No. 62/150,103, filed on Apr. 20, 2015.

(51) Int. Cl.
| | |
|---|---|
| *A61B 5/107* | (2006.01) |
| *G06T 7/00* | (2017.01) |
| *G06N 5/04* | (2006.01) |
| *G06K 9/46* | (2006.01) |
| *A61B 5/00* | (2006.01) |
| *G06T 7/33* | (2017.01) |

(52) U.S. Cl.
CPC .......... *A61B 5/1079* (2013.01); *A61B 5/0077* (2013.01); *A61B 5/1072* (2013.01); *A61B 5/742* (2013.01); *G06K 9/46* (2013.01); *G06N 5/046* (2013.01); *G06T 7/0014* (2013.01); *G06T 7/337* (2017.01); *A61B 5/486* (2013.01); *A61B 2503/12* (2013.01); *A61B 2560/0475* (2013.01); *G06T 2207/10016* (2013.01); *G06T 2207/30196* (2013.01)

(58) Field of Classification Search
CPC ... A61B 5/0077; A61B 5/1072; A61B 5/1079; A61B 5/486; A61B 5/742; A61B 2503/12; A61B 2560/0475; G06K 9/46; G06N 5/046; G06T 7/0014; G06T 7/337; G06T 2207/10016; G06T 2207/30196
See application file for complete search history.

(56) References Cited

U.S. PATENT DOCUMENTS

| | | | | |
|---|---|---|---|---|
| 7,567,914 B2 * | 7/2009 | Bonissone | ............. | G06Q 10/10 705/2 |
| 7,813,945 B2 * | 10/2010 | Bonissone | ............. | G06Q 40/02 705/4 |

(Continued)

*Primary Examiner* — Katrina Fujita
(74) *Attorney, Agent, or Firm* — Eric L. Sophir; Dentons US LLP

(57) ABSTRACT

A system and method for automated body mass index is disclosed. The disclosed method operates within a system architecture including one or more computing devices, one or more servers, and one or more databases. A processor operating within the one or more servers executes one or more algorithms for detecting relevant features associated with a potential client's multimedia information. The method may include calculating feature values, such as abdomen circumference, face width, face height, cheekbone width, jaw width, and neck width, and the like as well as calculating the body mass index of the potential client using one or more regression algorithms. A baseline and updated BMI may be determined, and used for determining a baseline and updated value.

22 Claims, 7 Drawing Sheets

(56) References Cited

U.S. PATENT DOCUMENTS

| | | | | |
|---|---|---|---|---|
| 8,214,314 B2* | 7/2012 | Bonissone | G06Q 40/00 706/20 |
| 8,510,133 B2* | 8/2013 | Peak | G06Q 40/08 705/2 |
| 9,224,171 B2* | 12/2015 | Peak | G06Q 40/08 |
| 2004/0236611 A1* | 11/2004 | Bonissone | G06Q 40/02 705/4 |
| 2005/0031080 A1* | 2/2005 | Klingenbeck-Regn | A61B 5/1072 378/95 |
| 2008/0091463 A1* | 4/2008 | Shakamuri | G06F 19/3431 705/2 |
| 2009/0150192 A1* | 6/2009 | Gore | G06Q 40/08 705/4 |
| 2010/0246898 A1* | 9/2010 | Izumi | A63B 6/00 382/106 |
| 2010/0312584 A1* | 12/2010 | Bradshaw | G06Q 50/24 705/4 |
| 2011/0004492 A1* | 1/2011 | Bradshaw | G06Q 50/24 705/4 |
| 2011/0004493 A1* | 1/2011 | Bradshaw | G06Q 50/24 705/4 |
| 2013/0211852 A1* | 8/2013 | Roizen | G06F 19/328 705/2 |
| 2014/0025346 A1* | 1/2014 | Uchiyama | A61B 5/744 703/1 |
| 2014/0039351 A1* | 2/2014 | Mix | A61B 5/1114 600/587 |
| 2014/0278491 A1* | 9/2014 | Weiss | G06Q 40/08 705/2 |
| 2015/0154453 A1* | 6/2015 | Wilf | G06K 9/00711 382/103 |
| 2015/0164399 A1* | 6/2015 | Beg | G06Q 10/10 600/301 |
| 2016/0093085 A1* | 3/2016 | Ray | A61B 5/6888 345/419 |
| 2016/0253798 A1* | 9/2016 | Barrett | A61B 5/0077 |
| 2017/0103677 A1* | 4/2017 | Bhattacharjee | G09B 5/02 |

* cited by examiner

SYSTEMS AND METHODS FOR AUTOMATED BODY MASS INDEX CALCULATION TO DETERMINE VALUE

CROSS-REFERENCE TO RELATED APPLICATIONS

This application claims priority to U.S. Provisional Patent Application Ser. No. 62/150,103, entitled "Systems and Methods for Automated Body Mass Index Calculation to Determine Underwriting Value for Insurance," filed Apr. 20, 2015, which is hereby incorporated by reference in its entirety.

FIELD OF THE DISCLOSURE

The present disclosure relates in general to data analytics, and more specifically to systems and methods for automated body mass index calculation.

BACKGROUND

Body mass index (BMI) is a wide known indicator employed in health insurance. Health insurance companies look at body mass index for insurance rating purposes for the reason that BMI is a significant factor correlated with health risk conditions, such as obesity and heart disease. Individuals applying for an insurance plan may be classified in different categories depending on their respective BMI, which may affect life insurance premiums set to the individuals.

Currently, many insurance companies require paramedical examiners to visit potential clients for the purpose of administering one or more tests, including BMI samples. BMI samples could include acquiring bodily fluids (e.g., blood, urine) from the potential clients. These tests imply potential delays in gathering the information required, and may be subject to human error. Although a BMI calculation requires only a few pieces of information from potential clients, such as height and weight, and potential clients are able to provide this information through any communication technology available, there is still a need to validate the information provided by the potential clients.

Thus, there is a need for providing systems methods to address these and other concerns.

SUMMARY

Systems and methods for an automated body mass index calculation are disclosed. In one embodiment, a system architecture may include components, such as one or more computing devices connected to one or more servers via a network connection. In this embodiment, the one or more servers include an analytical engine that coordinates multiple algorithms for data fetching, image processing tasks, and predictive analytics. The aforementioned algorithms may be executed by the server processor and/or the computing device processor. In one or more embodiments, the one or more servers are in communication with a database so that the analytical engine has access to relevant multimedia data associated with a potential client.

In another embodiment, a method for an automated body mass index calculation may include a computing device that allows an agent to request a body mass index calculation of a specific potential client. In this embodiment, the request is processed by a server. Further to this embodiment, the server is in communication with a database containing relevant multimedia information associated with a customer, and includes an analytical engine coordinating multiple algorithms. In one or more embodiments, the analytical engine includes a data extraction module and a data processing module. In these embodiments, the data extraction module fetches relevant multimedia information regarding a potential client, and makes the relevant multimedia information available to the data processing module. In one embodiment, the data processing module performs feature detection over the multimedia information, computes one or more feature values or feature vectors, normalizes the feature values, and uses the normalized feature values along with one or more regression algorithms for calculating the body mass index associated with a potential client.

One embodiment of a computer-implemented method may include receiving height and weight data of a potential customer. Upon receipt of the height and weight data, a request may be made for an image of the potential customer to be captured from a remote computing device, where the requested image includes a standard sized object positioned in the image according to at least one reference point. An image of the potential customer may be received, where the image is captured and transmitted from the remote computing device, where the image includes a standard sized object positioned in the image according to the at least one reference point. Upon receipt of the image, at least one anatomical region of the potential customer may be detected, a calculation of a feature value of the detected at least one anatomical region of the potential customer in comparison to the standard sized object positioned in the image according to the at least one reference point may be made, where the calculation includes utilizing at least one image processing technique on the detected at least one anatomical region of the potential customer and on the standard sized object positioned in the image according to the at least one reference point feature value, the feature value may be normalized, a body mass index (BMI) of the potential customer may be predicted based on the normalized feature value, and the BMI may be caused to be transmitted to a computing device. In transmitting the BMI, the BMI may be caused to be displayed on a graphical user interface.

One embodiment of a system and computerized-method may include receiving height and weight data of a potential customer. Upon receipt of the height and weight data, a request may be made for a first electronic image of the potential customer to be captured from an image capture device of the potential customer, where the requested image includes a standard sized object positioned in the image according to at least one reference point for the first image. An first electronic image of the potential customer may be received via a communications network from the image capture device of the potential customer at a first time, where the first image is captured and transmitted from the image capture device, where the first image includes a standard sized object positioned in the image according to the at least one reference point for the first image. A baseline body mass index (BMI) of the potential customer may be computed as a function of the height and weight data and the first image inclusive of the standard sized object positioned in the image according to the least one reference point for the first image. A determination of a baseline underwriting value (e.g., for an insurance policy) may be made as a function of the computed BMI for the potential customer (e.g., to be an insured under an insurance policy).

Updated height and weight data of the insured may be received at a second time. Upon receipt of the updated height and weight data, a request may be made for a second electronic image of the potential customer to be captured from the image capture device of the potential customer, where the requested image includes a standard sized object positioned in the image according to at least one reference point for the second image. A second electronic image of the potential customer may be received via the communications network from the image capture device of the potential customer at a second time, where the second image is captured and transmitted from the image capture device, where the second image includes a standard sized object positioned in the image according to the at least one reference point for the second image. The standard sized objects in the first and second images may be the same or different standard sized objects. An updated BMI of the insured may be computed as a function of the updated height and weight data and the second image inclusive of the standard sized object positioned in the image according to the least one reference point for the second image. A determination of an updated value (e.g., underwriting value) may be made (e.g., for an insurance policy) as a function of the computed updated BMI.

Numerous other aspects, features and benefits of the present disclosure may be made apparent from the following detailed description taken together with the drawing figures.

BRIEF DESCRIPTION OF THE DRAWINGS

The present disclosure can be better understood by referring to the following figures. The components in the figures are not necessarily to scale, emphasis instead being placed upon illustrating the principles of the disclosure. In the figures, reference numerals designate corresponding parts throughout the different views.

DETAILED DESCRIPTION

Figure 1:
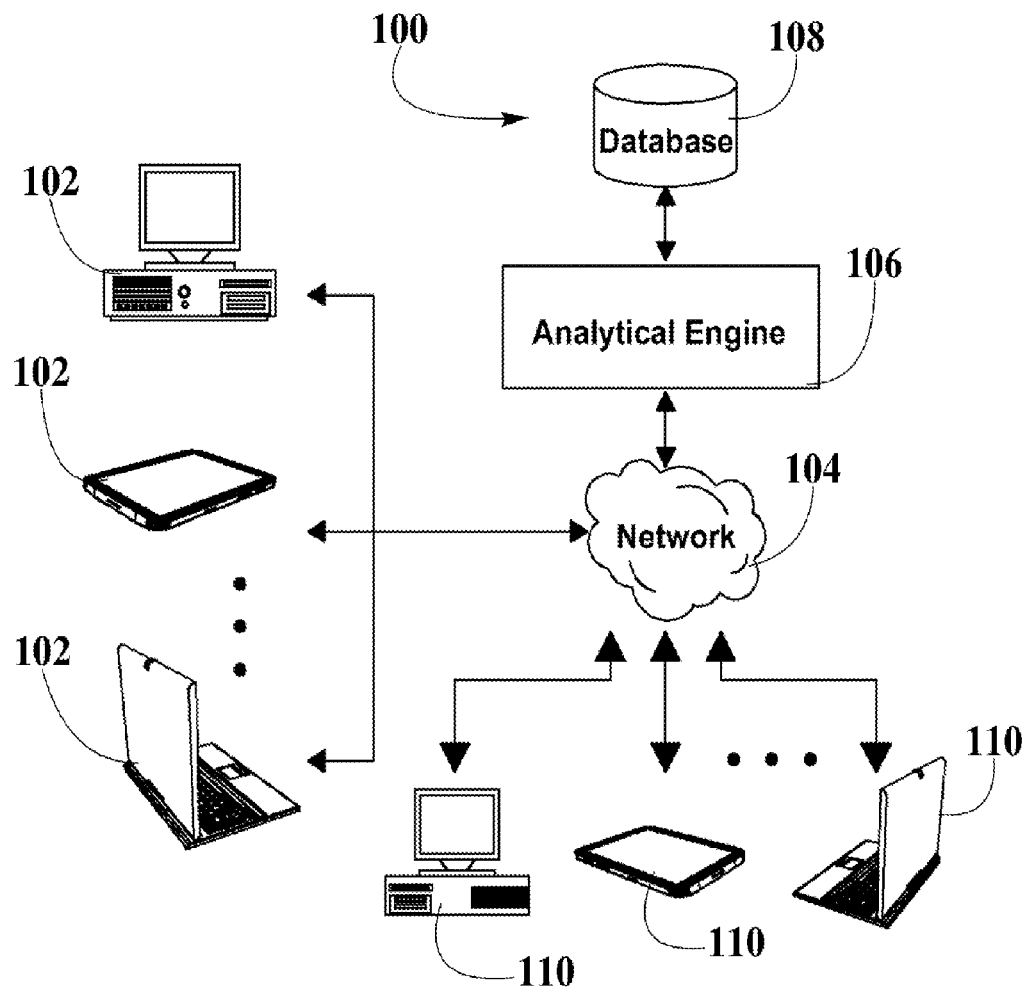
FIG. 1 is an illustrative system architecture for automated body mass index calculation of potential customers, according to an exemplary embodiment.

The present disclosure is here described in detail with reference to embodiments illustrated in the drawings, which form a part here. Other embodiments may be used and/or other changes may be made without departing from the spirit or scope of the present disclosure. The illustrative embodiments described in the detailed description are not meant to be limiting of the subject matter presented here.

As used here, the following terms may have the following definitions:

"Body mass index" refers to a measure of body fat based on height and weight, and which insurance companies may employ for insurance rating purposes.

"Feature" refers to a relevant piece of information that characterizes or that is correlated with the body mass index of a potential client.

"Feature detection" refers to the process of finding key points or features in an image.

"Feature value or vector" refers to the quantitative representation of one or more features resulting from one or more mathematical operations.

"Normalization" refers to adjusting feature values measured on different ranges to a notionally common scale.

"Image smoothing" refers to the process of reducing noise in an image in order to capture important patterns.

Reference will now be made to the exemplary embodiments illustrated in the drawings, and specific language will be used here to describe the same. It will nevertheless be understood that no limitation of the scope of the invention is thereby intended. Alterations and further modifications of the inventive features illustrated here, and additional applications of the principles of the inventions as illustrated here, which would occur to one skilled in the relevant art and having possession of this disclosure, are to be considered within the scope of the invention.

FIG. 1 is an illustrative system architecture 100 for performing an automated body mass index (BMI) calculation. System architecture 100 includes one or more client computing devices 102, network connection 104, analytical engine 106, one or more databases 108, and one or more computing devices 110.

In FIG. 1, client computing devices 102 are operatively in bi-directional communication with network connection 104. Network connection 104 is operatively in bi-directional communication with analytical engine 106. Analytical engine 106 may be operatively in bi-directional communication with database 108. Additionally, analytical engine 106 is operatively in bi-directional communication with computing devices 110.

In FIG. 1, client computing devices 102 may include smartphones, desktop computers, laptop computers, servers, tablets, PDAs, single computers with multiple processors, several networked computers, specialized hardware, and the like. In one embodiment, potential clients employ client computing devices 102 for collecting personal information, such as weight, height, pictures, and/or videos. In this embodiment, the personal information is sent to a company for further analysis, such as for capturing image(s) of a potential customer, a BMI calculation. In one or more embodiments, client computing devices 102 include one or more built-in cameras.

In one embodiment, client computing devices 102 perform one or more functions of a server. In this embodiment, client computing devices 102 are able to take pictures and videos, and store the pictures and videos in an internal memory. Further to this embodiment, the analytical engine 106 operates within client computing devices 102. Therefore, the client computing device's processor is able to execute software modules for data fetching, image processing, and BMI calculation.

In FIG. 1, network connection 104 is implemented as any type of suitable hardware, software, and/or firmware that interconnect and otherwise couple computing devices to allow effective communication between the aforementioned computing devices. Examples of network connection 104 include intranets, local area networks (LANs), virtual private networks (VPNs), wide area networks (WANs), the Internet, and the like.

In FIG. 1, analytical engine 106 may be configured as a collection of components that interact with each other in order to accept requests from agents and give responses accordingly. Analytical engine 106 additionally includes programming running to serve the requests of other programs, the client programs. Thus, the server performs some tasks on behalf of client programs. Examples of client programs running on analytical engine 106 includes programs designed and built to store potential customer data, process the potential customer data, perform one or more BMI calculations based on the potential customer data, and provide feedback to an agent through one or more computing devices 110.

Database 108 may be implemented as a relational database that stores information about both the data and how the data is related. In these embodiments, database 108 is implemented as conventional database management systems (DBMS), such as, MySQL, PostgreSQL, SQLite, Microsoft SQL Server, Microsoft Access, Oracle, SAP, dBASE, FoxPro, IBM DB2, LibreOffice Base, FileMaker Pro, MongoDb and/or any other type of database that may organize collections of data.

In one embodiment, data stored in database 108 includes potential customers' data such as pictures, videos, height and weight information, and the like. The potential customers' information is used as for automated BMI calculations, where BMI calculations include but are not limited to calculations based on image processing and predictive analytics as well as calculations based on potential customer information regarding height and weight.

In FIG. 1, computing devices 110 may include smartphones, desktop computers, laptop computers, servers, tablets, PDAs, single computer with multiple processors, several networked computers, specialized hardware, and the like. In one embodiment, computing devices 110 are used by an agent to perform duties associated with body mass index calculation.

In an illustrative operation, computing device 110 allows an agent to request for a BMI calculation related to a potential customer. Upon the agent's request, analytical engine 106 retrieves data related to the potential customer, such as one or more pictures as well as height and weight information. Next, analytical engine 106 may process the one or more images and employ one or more algorithms for determining the BMI of the potential customer. The BMI may be compared with the BMI calculated based on the potential customer height and weight information. In this example, the results are presented to the agent through client computing device 110.

The computing code running in system architecture 100 includes programs designed and built to perform automated BMI calculations. The computing code may process multiple elements simultaneously in multi-processor environments. Such a system configuration allows performing large work, such as heavy calculations and time consuming analysis, in a more efficient manner than other approaches, such as manual work performed by humans or approaches relying on a single computer. As will become apparent, functions and operations of system architecture 100 are sufficiently complex as to require implementation on a computer system, and cannot be performed in the human mind simply by mental steps.

In one embodiment, the aforementioned computing code is suited for processing multiple elements simultaneously to solve a problem in multi-processor environments. In this embodiment, computing devices 110 suitable for executing the computing code include a single computer with multiple processors, several networked computers, specialized hardware, or any combination of the aforementioned elements. Further to this embodiment, multi-processor environments include various architectures such as multi-core chips, clusters, field-programmable gate arrays (FPGAs), digital signal processing chips, and/or graphical processing units (GPUs). To this end, the computing code is parallelized for execution in a multi-processor environment including any number or combination of the above listed architecture types. The instruction sets suitable for parallel execution generated from the computing code allows multiple threads of computing code to be executed concurrently by the various computing elements in the multi-processor environment.

Figure 2:
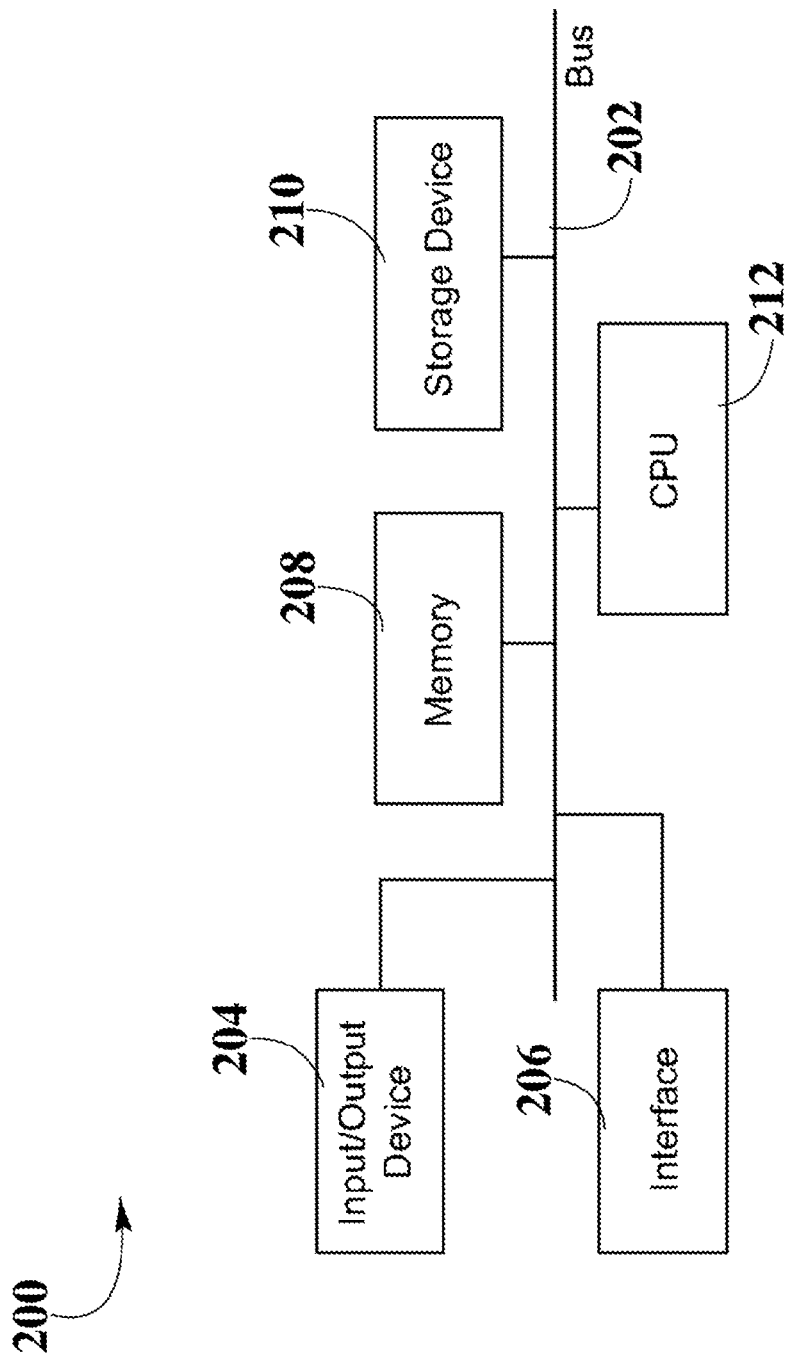
FIG. 2 is an illustrative computing device or server in which one or more embodiments of the present disclosure operate, according to an exemplary embodiment.

FIG. 2 is an exemplary computing device 200 or server in which one or more embodiments of the implementation operate, according to an embodiment. In one embodiment, computing device 200 includes bus 202, input/output (I/O) device 204, communication interface 206, memory 208, storage device 210 and central processing unit 212. In another embodiment, computing device 200 includes additional, fewer, different, or differently arranged components than those illustrated in FIG. 2.

In FIG. 2, bus 202 is in physical communication with I/O device 204, communication interface 206, memory 208, storage device 210, and central processing unit 212. Bus 202 includes a path that permits components within computing device 200 to communicate with each other. Examples of I/O device 204 include peripherals and/or other mechanisms that may enable an examiner or candidate to input information to computing device 200, including a keyboard, computer mice, buttons, touch screens, touch-pad, voice recognition, biometric mechanisms, and the like. I/O device 204 also includes a mechanism that outputs information to the examiner or candidate using computing device 200, such as, a display, a microphone, a light emitting diode (LED), a printer, a speaker, orientation sensors, and the like. The orientation sensors include one or more accelerometers, one or more gyroscopes, one or more compasses, and the like. The accelerometer provides a respective change of a respective angle about a respective axis. The gyroscope provides a respective rate of change of a respective angle about a respective axis and the compass provides a directional heading.

Examples of communication interface 206 include mechanisms that enable computing device 200 to communicate with other computing devices and/or systems through network connections. Examples of memory 208 include random access memory 208 (RAM), read-only memory (ROM), flash memory, and the like. Examples of storage device 210 include magnetic and/or optical recording medium, ferro-electric RAM (F-RAM) hard disks, solid-state drives, floppy disks, optical discs, and the like. In one embodiment, memory 208 and storage device 210 store information and instructions for execution by central processing unit 212. In another embodiment, central processing unit 212 includes a microprocessor, an application specific integrated circuit (ASIC), or a field programmable object array (FPOA), and the like. In this embodiment, central processing unit 212 interprets and executes instructions retrieved from memory 208 and storage device 210.

According to some aspects of this embodiment, computing device 200 is implemented as part of a server, client computing devices 102, computing devices 110, or other components of system architecture 100. Examples of these implementations include servers, authorized computing devices, smartphones, desktop computers, laptop computers, tablet computers, PDAs, another type of processor-controlled device that receives, processes, transmits digital data, and the like. Additionally, computing device 200 performs certain operations that are required for the proper operation of the systems and methods described herein. Suitable computing devices 200 perform these operations in response to central processing unit 212 executing software instructions contained in a computer-readable medium, such as memory 208.

In one embodiment, the software instructions of the system are read into memory 208 from another memory location, such as storage device 210, or from another computing device 200 (e.g., client computing devices 102, computing devices 110 and the like) via communication interface 206. In this embodiment, the software instructions contained within memory 208 cause central processing unit 212 to perform processes that will be described below in FIGS. 3-4.

Figure 3:
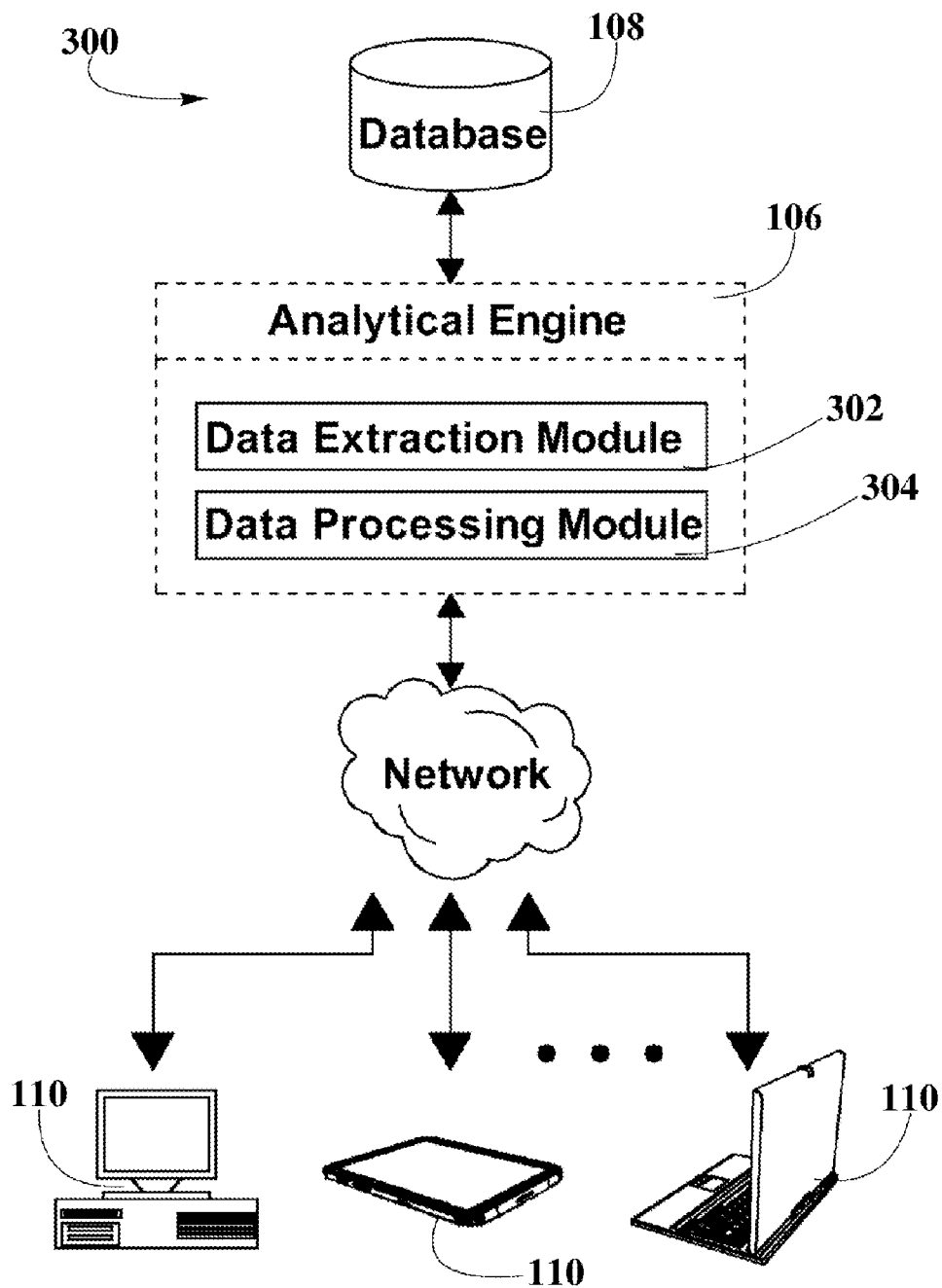
FIG. 3 is an illustrative block diagram of a sub-system of a portion of a system architecture pertaining to an analytical engine, according to an exemplary embodiment.

FIG. 3 is an illustrative block diagram of a sub-system 300 of a portion of system architecture 100 pertaining to analytical engine 106. In one embodiment, analytical engine 106 further includes data extraction module 302 and data processing module 304. Although analytical engine 106 includes the listed components, it should be understood that analytical engine 106 can include less components, more components, or different components depending on the desired analysis goals. In FIG. 3, analytical engine 106 is operatively coupled and in bi-directional communication with database 108.

In one embodiment, analytical engine 106 is implemented as one or more computer software modules that include programmatic rules or logic for analyzing data and calculating the body mass index (BMI) of a potential customer. In this embodiment, data extraction module 302 retrieves data related to the potential customer from database 108. The data is then processed by data processing module 304, which performs one or more image processing tasks and provides insight for determining the BMI of the potential customer. Further to this embodiment, the results derived from data processing module 304 may be presented through computing device 110, where computing device 110 previously requested the BMI calculation associated with the potential customer.

Data extraction module 302 is configured to retrieve data regarding a potential customer, where the data is stored in database 108. The data includes pictures, height and weight information, and the like. Next, data extraction module 302 feeds data processing module 304 with the data retrieved.

In one embodiment, data processing module 304 is configured to calculate the BMI of a potential customer based on predictive analytic techniques. The predictive analytic techniques rely on a set of relevant features derived from the potential customer's pictures and/or videos. In one embodiment, the predictive analytic techniques include feeding feature values of a large number of people ("large set of feature values") into a neural network so that the neural network can learn the large set of feature values and generate a predictive model and predicting feature values of the potential customer with the resulting neural network via the predictive model after it has learned the large set of feature values. In a particular embodiment, the predictive model is retrained according to active learning that involves storing a probability distribution of the large set of feature values, identifying areas in the probability distribution where there is not much knowledge or evidence, gathering data in the identified areas, and indicating the need to retrain the predictive model when enough data is gathered in the identified areas. The relevant features are derived using one or more image processing algorithms. Additionally, data processing module 304 is able to calculate the BMI of a customer using height and weight information.

In an illustrative operation, given a BMI calculation request, data extraction module 302 retrieves information related to a potential customer, such as one or more pictures as well as height and weight data. Next, data processing module 304 processes the one or more pictures, extracting one or more relevant features, and determines the BMI of the potential customer. The BMI can be compared with the BMI calculated based on the potential customer height and weight information. In this example, the results derived from data processing module 304 may be presented to an agent through computing device 110.

A plurality of methods implemented by analytical engine 106 are performed by one or more computing devices, such as computing device 200. The methods are implemented with components of the exemplary operating environments of FIGS. 1-3. The steps of this illustrative process are embodied in a computer readable medium containing a computer readable code such that the steps are implemented when the computer readable code is executed by a computing device. While the blocks in the disclosed process are shown in a particular order, the actual order may differ. In some embodiments, some steps are performed in parallel.

Figure 4A:
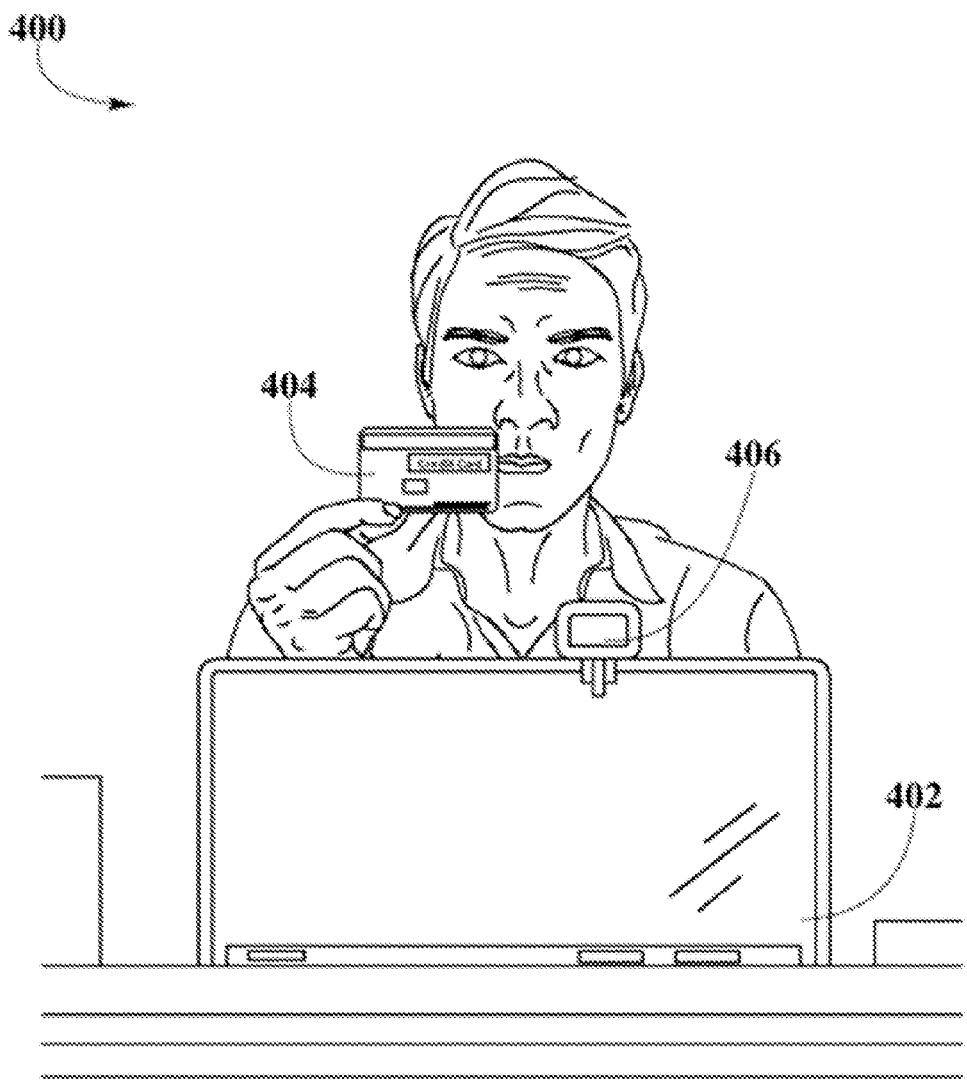
FIG. 4A is a diagram generally illustrating the front end of an illustrative system for automated body mass index, according to an exemplary embodiment.

FIG. 4A is an illustration 400 of a front end of an illustrative system for performing automated body mass index calculations. In one embodiment, illustration 400 includes client computing device 402, standard sized object 404, camera 406, and end user 408 (i.e., a potential customer).

In one embodiment, end user 408 employs client computing device 402 for collecting multimedia information that is later employed for performing an automated body mass index calculation. In this embodiment, end user 408 takes/captures one or more pictures holding standard sized object 404, such as an ID card, a credit card, a ruler, and the like, via a graphical user interface, implemented by a method 420 described below. Further to this embodiment, the standard sized object 404 provides a size reference that is employed in the calculation of one or more feature values. In one or more embodiments, the feature values are used for making BMI predictions. In some embodiments, end user 408 takes the one or more pictures using camera 406. In these embodiments, the one or more pictures are stored in client computing device 402 and can be sent to other components of a system architecture for performing an automated body mass index calculation through a network connection.

Figure 4B:
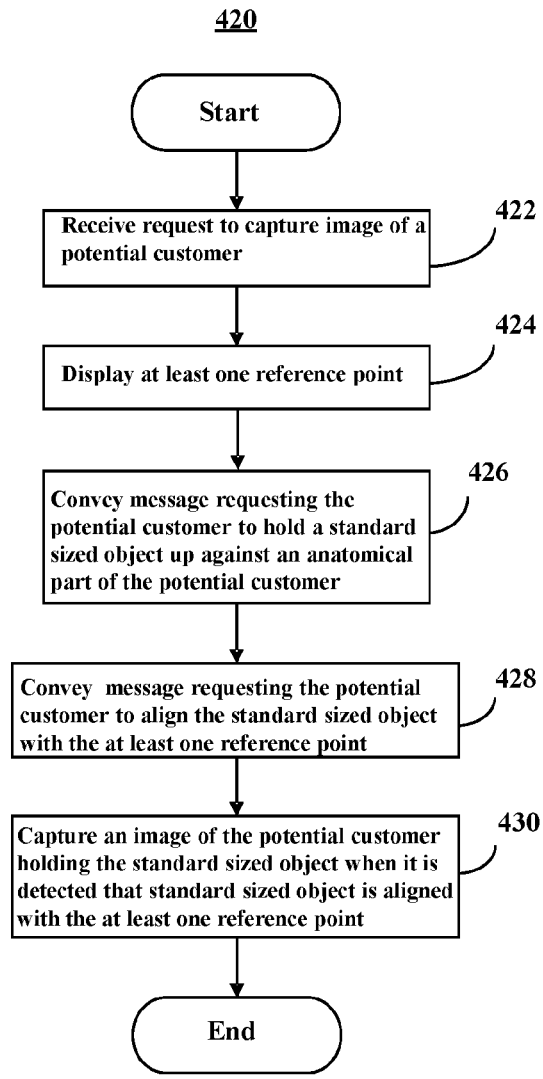
FIG. 4B is a flow diagram generally illustrating an illustrative method for taking one or more pictures of an end user holding standard sized object, according to another embodiment.

FIG. 4B is a flow diagram generally illustrating an illustrative method 420 for taking/capturing the one or more pictures of end user 408 holding standard sized object 404. The steps of the method are implemented with components of the illustrative operating environments of FIGS. 1-3. The steps of this illustrative method are embodied in a computer readable medium containing computer readable codes such that the steps are implemented when the computer readable code is executed by a computing device. In some implementations, certain steps of the method can be combined, performed simultaneously, or in a different order, without deviating from the objective of the method. The method starts at step 422, where a request is received to capture an image of end user 408. Method 420 then advances to step 424. At step 424, at least one reference point (e.g., a frame graphic, a rectangle graphic) is displayed. Method 420 then advances to step 426. At step 426, a message is conveyed requesting end user 408 to hold standard sized object 404 up against an anatomical part of end user 408 (e.g., face, chest). Method 420 then advances to step 428. At step 428, a message is conveyed requesting end user 408 to align standard sized object 404 with the at least one reference point. Method 420 then advances to step 430. At step 430, when it is detected that standard sized object 404 is aligned with the at least one reference point, an image of end user 408 holding standard sized object 404 is taken.

Figure 5:
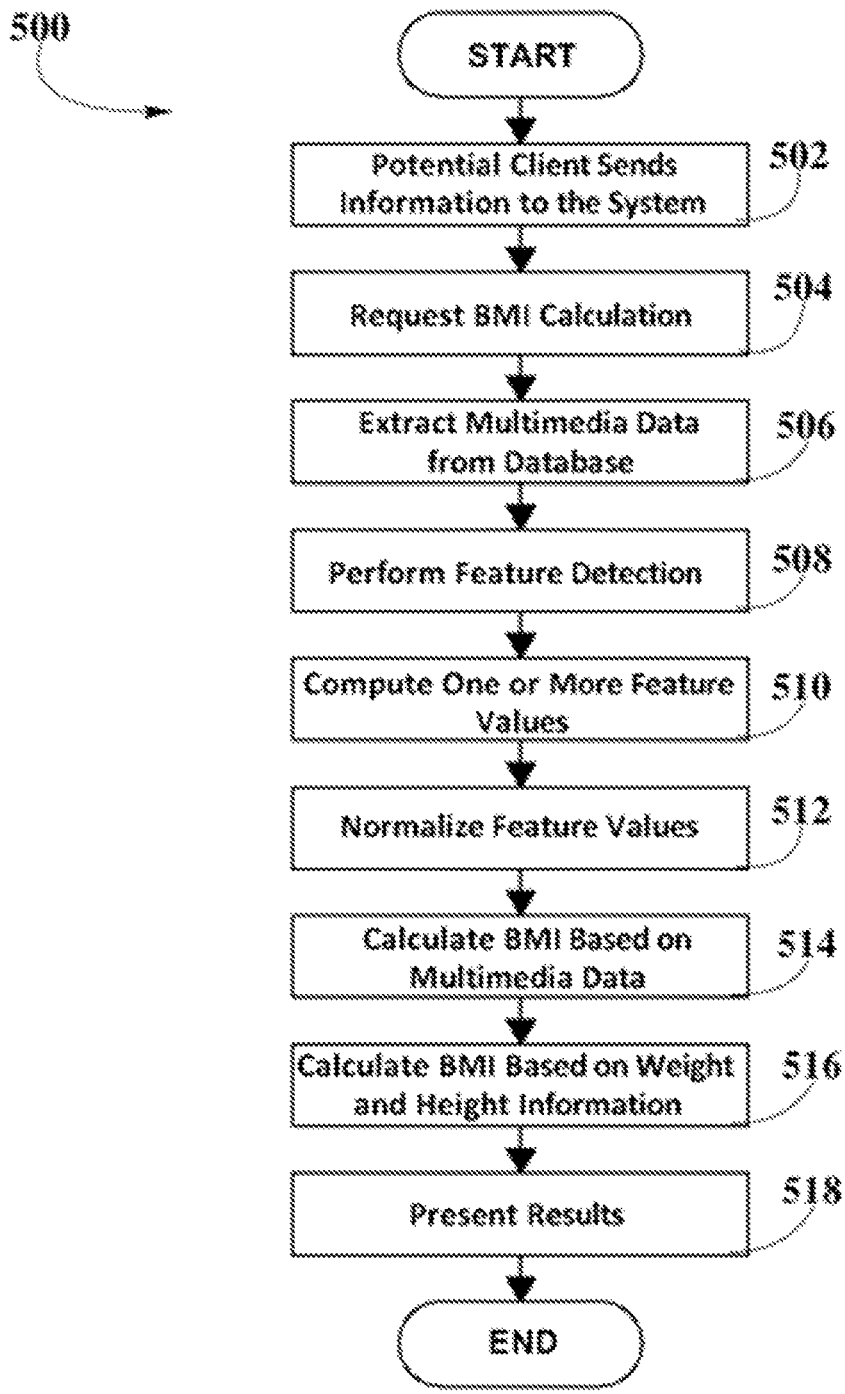
FIG. 5 is a flow diagram generally illustrating an illustrative method for automated body mass index calculation, according to another embodiment.

FIG. 5 is a flow diagram generally illustrating an illustrative method 500 for performing an automated body mass index calculation. The steps of the method are implemented with components of the illustrative operating environments of FIGS. 1-3. The steps of this illustrative method are embodied in a computer readable medium containing computer readable codes such that the steps are implemented when the computer readable code is executed by a computing device. In some implementations, certain steps of the method can be combined, performed simultaneously, or in a different order, without deviating from the objective of the method.

The method starts at step 502, where one or more client computing devices allow a potential client to provide personal information, such as weight and height, and multimedia data, such as, pictures and videos, to a system that performs automated body mass index calculations. In some embodiments, the multimedia data is provided to the system during a live interview with an agent. In other embodiments, the information provided by the potential client is stored in the system's database. In some embodiments, the multimedia data is captured using the elements and methods described in FIG. 5, below. Method 500 then advances to step 504.

In another embodiment, the agent is in a one-on-one online interaction with the potential client, where the agent requests one or more pictures and/or one or more videos from the potential client as well as weight and height information. The potential client takes one or more pictures and/or one or more videos using a client computing device and sends that information, along with other information, using a suitable network connection. The potential client's information is stored in the system's database. In yet another embodiment, the disclosed method operates in a client computing device, where the potential client's information is stored in the client computing devices' memory.

At step 504, an agent requests, through a computing device, the BMI calculation of a potential client. Method 500 then advances to step 506.

At step 506, the analytical engine employs a data extraction module for retrieving multimedia information regarding the potential client. Method 500 then advances to step 508.

At step 508, the analytical engine 106 detects one or more relevant features from the multimedia data. In an example and referring to FIG. 3, the feature detection step is performed by data processing module 304 of analytical engine 106. In one embodiment, the data processing module employs one or more computer vision or image processing algorithms for extracting relevant features from the multimedia data. Examples of algorithms for feature detection may include Adaboost classifier, Cany edge detector, Laplacian of Gaussian, determinant of hessian, and the like. Optionally, the data processing module employs one or more algorithms for image smoothing before step 508. Algorithms for image smoothing may include Gaussian kernel, Laplacian smoothing, low pass filtering, and the like. Method 500 then advances to step 510.

At step 510, the data processing module 304 performs one or more mathematical operations for calculating one or more feature values, such as abdomen circumference, face width, face height, cheekbone width, jaw width, neck width, ratio of face width to face height, distance between eyes, ratio of distance between of eyes to face width, total facial perimeter, ratio of width of upper face to width of lower face, eyes to nose distance, nose to mouth distance, structure of nose, and the like. In one embodiment, the calculation(s) of the feature value is assisted using pictures and/or videos including standard sized objects, such as rulers, credit cards, ID cards, and the like. In this embodiment, the standard sized objects provide a size reference that is employed in the calculation of the one or more feature values. Method 500 then advances to step 512.

At step 512, the data processing module 304 normalizes the feature values. In one or more embodiments, the normalization process modifies the feature values so that each feature contributes approximately proportionately to a prediction. Methods for normalization may include rescaling, standardization, scaling to unit length, and the like. Method 500 then advances to step 514.

At step 514, the data processing module 304 may predict or estimate the BMI associated to a potential client by using one or more regression algorithms. The regression algorithm(s) may include robust regression, k-Nearest Neighbors, support vector regression, Gaussian process regression, and the like. In one or more embodiments, the aforementioned regression algorithms utilize a training face using a suitable sample size of multimedia material. In one embodiment, the regression algorithms include feeding feature values of a large number of people ("large set of feature values") into a neural network so that the neural network can learn the large set of feature values and generate a predictive model and predicting feature values of the potential customer with the resulting neural network via the predictive model after it has learned the large set of feature values. In a particular embodiment, the predictive model is retrained according to active learning that involves storing a probability distribution of the large set of feature values, identifying areas in the probability distribution where there is not much knowledge or evidence, gathering data in the identified areas, and indicating the need to retrain the predictive model when enough data is gathered in the identified areas. Method 500 then advances to step 516.

At step 516, the data processing module 304 calculates the BMI using the potential client's information regarding weight and height. In one or more embodiments, the BMI is calculated using formula (1):

$$BMI = \frac{weight(kg)}{height(m)^2} \qquad (1)$$

In another embodiment, the data processing module calculates the BMI using formula (2):

$$BMI = \frac{weight(lb)}{height(in)^2} * 703 \qquad (2)$$

Method 500 then advances to step 518.

At step 518, the analytical engine 106 presents the results to the agent through a computing device. In one embodiment, the results include (i) the BMI calculated from the potential client's entered weight and height, (ii) the BMI calculated based on the multimedia information, and (iii) a delta value indicating an arithmetical difference between both BMI. In some embodiments, the results provide the agent with a better indicator regarding the potential client's actual BMI and the potential health risks associated with the actual BMI.

In one or more embodiments, the analytical engine 106 operates in a client computing device. Therefore, the client computing device's processor executes one or more software modules for data fetching, image processing, and BMI calculation. The BMI information is shared with the system's database through a network connection.

In an example and referring to FIG. 5, an agent interested in calculating the body mass index (BMI) of a potential client uses a client computing device in order to request the BMI of a potential client. Analytical engine 106 operating within one or more servers employs one or more algorithms for extracting multimedia information associated with the potential client. Afterwards, analytical engine 106 employs computer vision and regression algorithms for calculating the BMI of the potential client which may be 23.1. This BMI may correspond to a person with normal weight. The agent compares this BMI with the BMI calculated from information (such as weight and height) provided by the potential client. In this example, the BMI calculated from the clients' personal information is 23. The agent realizes that both BMI are consistent and that the potential client's weight does not represent a risk for health. This information is later employed for insurance rating purposes.

In another example and referring to FIG. 5, an agent and a potential client are conducting a video call. The agent requests one or more pictures and/or videos from the potential client as well as information regarding weight and height. The potential client employs a client computing device for taking one or more pictures and/or videos during the video call and delivers the information to the agent through a suitable network connection. The agent performs a BMI calculation request through a user interface. The agent determines that the BMI calculated based on the multimedia information and the BMI calculated based on the potential client's weight and height are consistent and both indicate that the potential client is underweight.

In yet another example and referring to FIG. 5, an agent interested in calculating the body mass index (BMI) of a potential client employs a client computing device in order to request the BMI of a potential client. Analytical engine 106, operating within one or more servers, employs one or more algorithms for extracting multimedia information associated with the potential client. Next, analytical engine 106 employs computer vision and regression algorithms for calculating the BMI of the potential client, which is 26. This BMI corresponds to an obese person. The agent compares this BMI with the BMI calculated based on the potential client's weight and height. The BMI is 19, which corresponds to a person with normal weight. The agent concludes that both BMI are not consistent and that a further validation of the potential client's information may be required.

By executing method 500 through the exemplary operating environments shown in FIGS. 1-3, big data analytics and data mining techniques can be implemented for a more efficient and faster processing of larger data sets. In this way, efficiencies are created by providing ways to automatically calculate and validate BMI of potential customers. These features allow performing large work, such as heavy calculations and time consuming analysis, in a more efficient manner than other approaches, such as manual work performed by humans.

One embodiment of a computer-implemented method may include receiving height and weight data of a potential customer. Upon receipt of the height and weight data, a request may be made for an image of the potential customer to be captured from a remote computing device, where the requested image includes a standard sized object positioned in the image according to at least one reference point. An image of the potential customer may be received, where the image is captured and transmitted from the remote computing device, where the image includes a standard sized object positioned in the image according to the at least one reference point. Upon receipt of the image, at least one anatomical region of the potential customer may be detected, a calculation of a feature value of the detected at least one anatomical region of the potential customer in comparison to the standard sized object positioned in the image according to the at least one reference point may be made, where the calculation includes utilizing at least one image processing technique on the detected at least one anatomical region of the potential customer and on the standard sized object positioned in the image according to the at least one reference point feature value, the feature value may be normalized, a body mass index (BMI) of the potential customer may be predicted based on the normalized feature value, and the BMI may be caused to be transmitted to a computing device. In transmitting the BMI, the BMI may be caused to be displayed on a graphical user interface.

In one embodiment, the standard sized object may be a credit card. Other standard sized objects may alternatively be utilized. The image may also include at least a partially unclothed, upper torso of the potential customer. The BMI may be calculated using only the height and weight data of the potential customer, and a delta value may be calculated between (i) the BMI calculated using only the height and weight data and (ii) the BMI predicted using the normalized feature value. The delta value may be presented. In an embodiment, the delta value may be presented to an agent. In predicting the BMI, a regression algorithm may be computed, and the regression algorithm may be trained by using a set of faces associated with individuals with respective known BMIs.

In one aspect, BMI of the potential customer may be calculated using only the height and weight data of the potential customer, and a determination of a category of life insurance of which the potential customer qualifies may be based on the BMI calculated using only the height and weight data. The image may be captured by a computing device with an integrated camera, such as a smartphone or other computing device. In one embodiment, the image may be a video image during a real-time video call. In an embodiment, the real-time video call may be with an agent. Detection of the anatomical region(s) may include detecting the anatomical region(s) utilizing at least one edge detector on the image. A determination of a dimension of the anatomical region(s) of the potential customer may be made.

Figure 6:
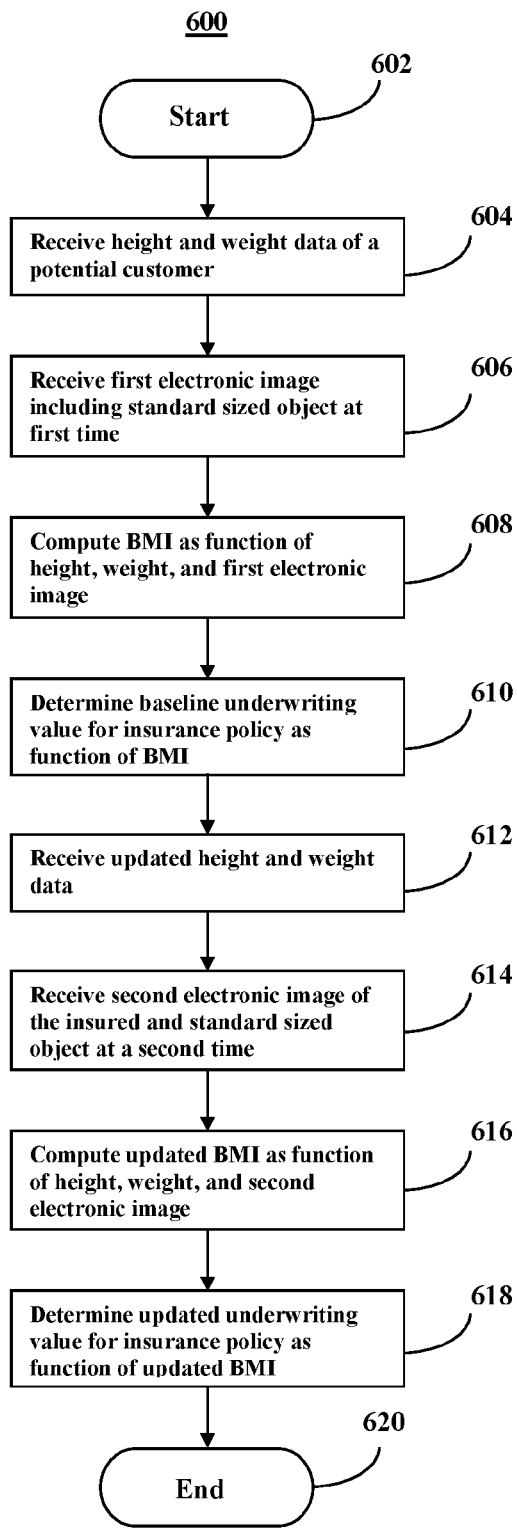
FIG. 6 is a flow diagram of an illustrative process for underwriting a potential customer for an insurance policy, according to an exemplary embodiment.

With regard to FIG. 6, a flow diagram of an illustrative process 600 for underwriting a potential customer for an insurance policy is presented. The process 600 is a computerized-method that is to be executed by a computing system, such as a computing system executing the analytical engine 106 as shown in FIG. 3, and processing unit being operated by the computing system. The process may start at step 602. Height and weight data of a potential customer may be received at step 604. In receiving the height and weight data, the data may be received from the potential customer entering the information via a user interface, such as a website, accessed by a computer, mobile device (e.g., tablet computer), or other communications device. Alternatively, the data may be received by an agent who receives the information in any form, such as via a telephone, or otherwise. At step 606, a first electronic image may be received via a communications network from an image capture device of the potential customer at a first time. The first image may be inclusive of a standard sized object. The standard sized object may be a credit card or otherwise. At step 608, a baseline body mass index (BMI) of the potential customer may be computed as a function of (i) the height and weight data and (ii) the first electronic image of the potential customer inclusive of the standard sized object. As an example, the computation may measure the standard sized object to determine scaling, skew, angle, and any other image information from the standard sized object so that anatomical regions of the potential customer can be accurately adjusted and measured.

At step 610, a baseline underwriting value for an insurance policy may be determined as a function of the computed BMI for the potential customer to be an insured under the insurance policy. That is, the baseline underwriting value may use the BMI of the potential customer as part of the calculation of the baseline underwriting value, and may include a variety of other factors, as well. The baseline underwriting value may be a first underwriting value for new or renewal potential customers who have not been processed using the imaging process described herein, for example.

At step 612, updated height and weight data of the insured may be received at a second time. The second time may be some period of time, such as one year or other time period, after the first time or into an insurance policy that would enable the insured to receive a discount or improved insurance plan as a result of improving his or her BMI. At step 614, a second electronic image may be received via the communications network from the image capture device of the insured at the second time. The second electronic image may be inclusive of a standard sized object. In one embodiment, the standard sized object may be the same standard sized object or same type of standard sized object (e.g., two different credit cards). In an alternative embodiment, the standard sized object may be a different standard sized object than the standard sized object used for determining the baseline BMI. For example, a ruler may be used for determining the updated BMI as compared to a credit card used for determining the baseline BMI. At step 616, an updated BMI of the insured may be computed as a function of the updated height and weight data and the second electronic image of the insured. At step 618, an updated underwriting value for the insurance policy may be determined as a function of the computed updated BMI.

One embodiment of a system and computerized-method may include receiving height and weight data of a potential customer. Upon receipt of the height and weight data, a request may be made for a first electronic image of the potential customer to be captured from an image capture device of the potential customer, where the requested image includes a standard sized object positioned in the image according to at least one reference point for the first image. An first electronic image of the potential customer may be received via a communications network from the image capture device of the potential customer at a first time, where the first image is captured and transmitted from the image capture device, where the first image includes a standard sized object positioned in the image according to the at least one reference point for the first image. A baseline body mass index (BMI) of the potential customer may be computed as a function of the height and weight data and the first image inclusive of the standard sized object positioned in the image according to the least one reference point for the first image. A determination of a baseline underwriting value (e.g., for an insurance policy) may be made as a function of the computed BMI for the potential customer (e.g., to be an insured under an insurance policy).

Updated height and weight data of the insured may be received at a second time. Upon receipt of the updated height and weight data, a request may be made for a second electronic image of the potential customer to be captured from the image capture device of the potential customer, where the requested image includes a standard sized object positioned in the image according to at least one reference point for the second image. A second electronic image of the potential customer may be received via the communications network from the image capture device of the potential customer at a second time, where the second image is captured and transmitted from the image capture device, where the second image includes a standard sized object positioned in the image according to the at least one reference point for the second image. The standard sized objects in the first and second images may be the same or different standard sized objects. An updated BMI of the insured may be computed as a function of the updated height and weight data and the second image inclusive of the standard sized object positioned in the image according to the least one reference point for the second image. A determination of an updated value (e.g., underwriting value) may be made (e.g., for an insurance policy) as a function of the computed updated BMI.

One embodiment of a system and computerized-method may include receiving height and weight data of a potential customer. Upon receipt of the height and weight data, a request may be made for a first electronic image of the potential customer to be captured from an image capture device of the potential customer, where the requested image includes a standard sized object positioned in the image according to at least one reference point for the first image. An first electronic image of the potential customer may be received via a communications network from the image capture device of the potential customer at a first time, where the first image is captured and transmitted from the image capture device, where the first image includes a standard sized object positioned in the image according to the at least one reference point for the first image. A baseline body mass index (BMI) of the potential customer may be computed as a function of the height and weight data and the first image inclusive of the standard sized object positioned in the image according to the least one reference point for the first image. A determination of a baseline underwriting value (e.g., for an insurance policy) may be made as a function of the computed BMI for the potential customer (e.g., to be an insured under an insurance policy).

Updated height and weight data of the insured may be received at a second time. Upon receipt of the updated height and weight data, a request may be made for a second electronic image of the potential customer to be captured from the image capture device of the potential customer, where the requested image includes a standard sized object positioned in the image according to at least one reference point for the second image. A second electronic image of the potential customer may be received via the communications network from the image capture device of the potential customer at a second time, where the second image is captured and transmitted from the image capture device, where the second image includes a standard sized object positioned in the image according to the at least one reference point for the second image. The standard sized objects in the first and second images may be the same or different standard sized objects. An updated BMI of the insured may be computed as a function of the updated height and weight data and the second image inclusive of the standard sized object positioned in the image according to the least one reference point for the second image. A determination of an updated value (e.g., underwriting value) may be made (e.g., for an insurance policy) as a function of the computed updated BMI.

In computing the baseline BMI, the process 600 may include detecting at least one anatomical region of the potential customer from the first electronic image. A feature value of the detected anatomical region(s) of the potential customer may be calculated, and the feature value may be normalized. The baseline BMI may be calculated as a function of the normalized feature value. In normalizing the feature value, the feature may be rotated, scaled, skewed, or other mathematical function(s) may be applied based on the standard sized object to cause the feature value to be consistent with real-world sizing so that BMI calculations may be more accurate. Other normalization process(es) may be utilized, as well.

Updating the updated BMI may include detecting at least one anatomical region of the insured from the second electronic image. The anatomical region may be the same anatomical region as used for determining the baseline BMI. Alternatively, the anatomical region may be another anatomical region as used for determining the baseline BMI. A feature value of the detected at least one anatomical region of the potential customer may be calculated and normalized, as previously described. Calculating the baseline BMI may include calculating the updated BMI as a function of the normalized feature value.

The process 600 may further include determining a baseline premium for the insurance policy based on the baseline underwriting value. Determining an updated premium for the insurance policy by may include determining that the updated BMI is an improvement over the baseline BMI, and, in response to determining that the updated BMI is an improvement over the baseline BMI, a determination of the updated premium to be lower than the baseline premium may be made. If a determination is made that the updated BMI is not an improvement over the baseline BMI, then a determination of the updated premium to be the same as the baseline premium may be made, The determination of a baseline underwriting value for an insurance policy may include determining a baseline underwriting value for a life insurance policy. In one embodiment, a notification date for notifying the insured to submit another image may be set. The notification date may be within one year of setting the baseline premium. A communication of a notification to the insured to submit another image on the notification date may be made. In response to receiving additional updated height and weight data of the insured and an additional image of the insured, computing, by the processing unit, an additional updated BMI of the insured may be made as a function of the additional updated height and weight data and the additional updated image of the insured. A determination of an additional updated underwriting value for the insurance policy may be made as a function of the computed additional updated BMI. A determination of an additional updated premium for the insurance policy based on the additional updated underwriting value may be made. A determination may be made for a baseline premium for the potential customer based on the baseline underwriting value, and a determination of an updated premium for the insurance policy may be made based on the updated underwriting value. Computing the baseline BMI and updated BMI may further include image processing the respective first and second electronic images using the respective standard sized objects to determine a scale of the image to enable at least one anatomical region to be scaled and measured. In addition to scaling, other image processing, such as determining a skew, angle, orientation, or any other image processing technique may be utilized.

The foregoing method descriptions and the process flow diagrams are provided merely as illustrative examples and are not intended to require or imply that the steps of the various embodiments must be performed in the order presented. As will be appreciated by one of skill in the art, the steps in the foregoing embodiments may be performed in any order. Words such as "then," "next," etc. are not intended to limit the order of the steps; these words are simply used to guide the reader through the description of the methods. Although process flow diagrams may describe the operations as a sequential process, many of the operations may be performed in parallel or concurrently. In addition, the order of the operations may be re-arranged. A process may correspond to a method, a function, a procedure, a subroutine, a subprogram, etc. When a process corresponds to a function, its termination may correspond to a return of the function to the calling function or the main function.

The various illustrative logical blocks, modules, circuits, and algorithm steps described in connection with the embodiments disclosed here may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

Embodiments implemented in computer software may be implemented in software, firmware, middleware, microcode, hardware description languages, or any combination thereof. A code segment or machine-executable instructions may represent a procedure, a function, a subprogram, a program, a routine, a subroutine, a module, a software package, a class, or any combination of instructions, data structures, or program statements. A code segment may be coupled to and/or in communication with another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

The actual software code or specialized control hardware used to implement these systems and methods is not limiting of the invention. Thus, the operation and behavior of the systems and methods were described without reference to the specific software code being understood that software and control hardware can be designed to implement the systems and methods based on the description here.

When implemented in software, the functions may be stored as one or more instructions or code on a non-transitory computer-readable or processor-readable storage medium. The steps of a method or algorithm disclosed here may be embodied in a processor-executable software module which may reside on a computer-readable or processor-readable storage medium. A non-transitory computer-readable or processor-readable media includes both computer storage media and tangible storage media that facilitate transfer of a computer program from one place to another. A non-transitory processor-readable storage media may be any available media that may be accessed by a computer. By way of example, and not limitation, such non-transitory processor-readable media may comprise RAM, ROM, EEPROM, CD-ROM or other optical disk storage, magnetic disk storage or other magnetic storage devices, or any other tangible storage medium that may be used to store desired program code in the form of instructions or data structures and that may be accessed by a computer or processor. Disk and disc, as used here, include compact disc (CD), laser disc, optical disc, digital versatile disc (DVD), floppy disk, and Blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and/or instructions on a non-transitory processor-readable medium and/or computer-readable medium, which may be incorporated into a computer program product.

The preceding description of the disclosed embodiments is provided to enable any person skilled in the art to make or use the present invention. Various modifications to these embodiments will be readily apparent to those skilled in the art, and the generic principles defined here may be applied to other embodiments without departing from the spirit or scope of the invention. Thus, the present invention is not intended to be limited to the embodiments shown here but is to be accorded the widest scope consistent with the following claims and the principles and novel features disclosed here.

What is claimed is:

1. A computerized-method comprising:
    upon receiving, by a processing unit, height and weight data of a potential customer, requesting, by the processing unit, a first electronic image of the potential customer to be captured from an image capture device of the potential customer, the requested first electronic image being inclusive of a standard sized object positioned in the first electronic image according to at least one reference point for the first electronic image;
    receiving, by the processing unit, the first electronic image of the potential customer via a communications network from the image capture device of the potential customer at a first time, wherein the first electronic image is captured and transmitted from the image capture device, the image being inclusive of the standard sized object positioned in the first electronic image according to the least one reference point for the first electronic image;
    computing, by the processing unit, a baseline body mass index (BMI) of the potential customer as a function of the height and weight data and the first electronic image inclusive of the standard sized object positioned in the image according to the least one reference point for the first electronic image;
    determining, by the processing unit, a baseline value as a function of the computed BMI for the potential customer;
    upon receiving, by the processing unit, updated height and weight data of the potential customer at a second time, requesting, by the processing unit, a second electronic image of the potential customer to be captured from the image capture device of the potential customer, the requested second electronic image being inclusive of a standard sized object positioned in the second electronic image according to at least one reference point for the second electronic image;
    receiving, by the processing unit, the second electronic image of the potential customer via the communications network from the image capture device of the potential customer at the second time, wherein the second electronic image is captured and transmitted from the image capture device, the second electronic image being inclusive of a standard sized object positioned in the second electronic image according to the least one reference point for the second electronic image;
    computing, by the processing unit, an updated BMI of the potential customer as a function of the updated height and weight data and the second electronic image inclusive of the standard sized object positioned in the second electronic image according to the least one reference point for the second electronic image; and
    determining, by the processing unit, an updated value as a function of the computed updated BMI.

2. The computerized-method of claim 1, wherein the standard sized object used for the first and second electronic images are the same.

3. The computerized-method of claim 1, wherein computing the baseline BMI comprises:
    detecting, by the processing unit, at least one anatomical region of the potential customer from the first electronic image;
    calculating, by the processing unit, a feature value of the detected at least one anatomical region of the potential customer;
    normalizing, by the processing unit, the feature value; and
    wherein calculating the baseline BMI includes calculating the baseline BMI as a function of the normalized feature value.

4. The computerized-method of claim 3, wherein computing the updated BMI comprises:
    detecting, by the processing unit, at least one anatomical region of the potential customer from the second electronic image;
    calculating, by the processing unit, a feature value of the detected at least one anatomical region of the potential customer;
    normalizing, by the processing unit, the feature value; and
    wherein calculating the updated BMI includes calculating the updated BMI as a function of the normalized feature value.

5. The computerized-method of claim 1, further comprising:
    determining a baseline premium based on the baseline value; and
    determining an updated premium by
        determining, by the processing unit, that the updated BMI is an improvement over the baseline BMI and in response to determining that the updated BMI is an improvement over the baseline BMI, determining the updated premium to be lower than the baseline premium, otherwise, determining the updated premium is the same as the baseline premium.

6. The computerized-method of claim 1, further comprising:
setting, by the processing unit, a notification date for notifying the potential customer to submit another image; and
communicating, by the processing unit, a notification to the potential customer to submit another image on the notification date.

7. The computerized-method of claim 1, further comprising:
in response to receiving additional updated height and weight data of the potential customer and an additional image of the potential customer, computing, by the processing unit, an additional updated BMI of the potential customer as a function of the additional updated height and weight data and the additional updated image of the potential customer;
determining, by the processing unit, an additional updated value as a function of the computed additional updated BMI; and
determining, by the processing unit, an additional updated premium based on the additional updated value.

8. The computerized-method of claim 1, further comprising:
determining, by the processing unit, a baseline premium for the potential customer based on the baseline value; and
determining, by the processing unit, an updated premium based on the updated value.

9. The computerized-method of claim 1, wherein computing the baseline BMI and updated BMI further comprises image processing, by the processing unit, the respective first and second electronic images using the respective standard sized objects to determine a scale of the image to enable at least one anatomical region to be scaled and measured.

10. The computerized-method of claim 1, wherein receiving the first electronic image being inclusive of the standard sized object positioned in the first electronic image according to the least one reference point for the first electronic image comprises:
receiving, by the image capture device, a request to capture an image of the potential customer;
displaying, by the image capture device, the at least one reference point for the first electronic image;
conveying, by the image capture device, a message requesting the potential customer to hold the standard sized object up against an anatomical part of the potential customer;
conveying, by the image capture device, a message requesting the potential customer to align the standard sized object with the at least one reference point for the first electronic image; and
capturing, by the image capture device, an image of the potential customer holding the standard sized object when it is detected, by the image capture device, that the standard sized object is aligned with the at least one reference point for the first electronic image.

11. The computerized-method of claim 1, wherein receiving the second electronic image being inclusive of the standard sized object positioned in the second electronic image according to the least one reference point for the second electronic image comprises:
receiving, by the image capture device, a request to capture an image of the potential customer;
displaying, by the image capture device, the at least one reference point for the second electronic image;
conveying, by the image capture device, a message requesting the potential customer to hold the standard sized object up against an anatomical part of the potential customer;
conveying, by the image capture device, a message requesting the potential customer to align the standard sized object with the at least one reference point for the second electronic image; and
capturing, by the image capture device, an image of the potential customer holding the standard sized object when it is detected, by the image capture device, that the standard sized object is aligned with the at least one reference point for the second electronic image.

12. A system comprising:
a memory unit;
an input/output unit; and
a processing unit in communications with said memory unit and input/output unit, and configured to
receive height and weight data of a potential customer,
request a first electronic image of the potential customer to be captured from an image capture device of the potential customer, the requested first electronic image being inclusive of a standard sized object positioned in the first electronic image according to at least one reference point for the first electronic image,
receive a first electronic image via a communications network from the image capture device of the potential customer at a first time, wherein the first electronic image is captured and transmitted from the image capture device, the first electronic image being inclusive of the standard sized object positioned in the first electronic image according to the least one reference point for the first electronic image,
compute a baseline body mass index (BMI) of the potential customer as a function of the height and weight data and the first electronic image inclusive of the standard sized object positioned in the first electronic image according to the least one reference point for the first electronic image,
determine a baseline underwriting value as a function of the computed BMI for the potential customer,
receive updated height and weight data of the insured at a second time,
request a second electronic image of the potential customer to be captured from the image capture device of the potential customer, the requested second electronic image being inclusive of a standard sized object positioned in the second electronic image according to at least one reference point for the second electronic image,
receive a second electronic image via the communications network from the image capture device of the insured at the second time, wherein the second electronic image is captured and transmitted from the image capture device, the second electronic image being inclusive of a standard sized object positioned in the electronic image according to the least one reference point for the second electronic image,
compute an updated BMI of the potential customer as a function of the updated height and weight data and the second image inclusive of the standard sized object positioned in the second electronic image according to the least one reference point for the second electronic image, and determine an updated value for the insurance policy as a function of the computed updated BMI.

13. The system of claim 12, wherein the standard sized object used for the first and second electronic images are the same.

14. The system of claim 12, wherein said processing unit, in computing the baseline BMI, is configured to
    detect at least one anatomical region of the potential customer from the first electronic image,
    calculate a feature value of the detected at least one anatomical region of the potential customer, and
    normalize the feature value,
    wherein the baseline BMI calculation is performed as a function of the normalized feature value.

15. The system of claim 14, wherein said processing unit, in computing the updated BMI, is configured to
    detect at least one anatomical region of the insured from the second electronic image,
    calculate a feature value of the detected at least one anatomical region of the potential customer, and
    normalize the feature value,
    wherein the updated BMI calculation is performed by calculating the updated BMI as a function of the normalized feature value.

16. The system of claim 12, wherein said processing unit is further configured to
    determine a baseline premium based on the baseline value and
    determine an updated premium, wherein said processing unit, in determining the updated premium is configured to
        determine that the updated BMI is an improvement over the baseline BMI, and
        in response to determining that the updated BMI is an improvement over the baseline BMI, determine the updated premium to be lower than the baseline premium, otherwise, determine the updated premium is the same as the baseline premium.

17. The system of claim 12, wherein said processing unit is further configured to
    set a notification date for notifying the potential customer to submit another image, and
    communicate a notification to the potential customer to submit another image on the notification date.

18. The system of claim 12, wherein said processing unit is further configured to
    compute an additional updated BMI of the potential customer in response to receiving and as a function of additional updated height and weight data of the potential customer and additional updated electronic image of the potential customer,
    determine an additional updated value as a function of the computed additional updated BMI, and
    determine an additional updated premium based on the additional updated value.

19. The system of claim 12, wherein said processing unit is further configured to
    determine a baseline premium for the potential customer based on the baseline value, and
    determine an updated premium based on the updated value.

20. The system of claim 12, wherein said processing unit, in computing the baseline BMI and updated BMI, is further configured to image process the respective first and second electronic images using the respective standard sized objects to determine a scale of the image to enable at least one anatomical region to be scaled and measured.

21. The system of claim 12, wherein the image capture device is configured to
    receive a request to capture an image of the potential customer,
    display the at least one reference point for the first electronic image,
    convey to the potential customer a message requesting the potential customer to hold the standard sized object up against an anatomical part of the potential customer,
    convey to the potential customer a message requesting the potential customer to align the standard sized object with the at least one reference point for the first electronic image, and
    capture an image of the potential customer holding the standard sized object when it is detected, by the image capture device, that the standard sized object is aligned with the at least one reference point for the first electronic image.

22. The system of claim 12, wherein the image capture device is configured to
    receive a request to capture an image of the potential customer,
    display the at least one reference point for the second electronic image,
    convey to the potential customer a message requesting the potential customer to hold the standard sized object up against an anatomical part of the potential customer,
    convey to the potential customer a message requesting the potential customer to align the standard sized object with the at least one reference point for the second electronic image, and
    capture an image of the potential customer holding the standard sized object when it is detected, by the image capture device, that the standard sized object is aligned with the at least one reference point for the second electronic image.

\* \* \* \* \*